(12) United States Patent
Synowicki et al.

(10) Patent No.: US 7,777,883 B2
(45) Date of Patent: *Aug. 17, 2010

(54) ELLIPSOMETRIC INVESTIGATION OF ANISOTROPIC SAMPLES

(75) Inventors: Ronald A. Synowicki, Lincoln, NE (US); Thomas E. Tiwald, Lincoln, NE (US)

(73) Assignee: J.A. Woollam Co., Inc., Lincoln, NE (US)

( * ) Notice: Subject to any disclaimer, the term of this patent is extended or adjusted under 35 U.S.C. 154(b) by 220 days.

This patent is subject to a terminal disclaimer.

(21) Appl. No.: 12/157,407

(22) Filed: Jun. 10, 2008

(65) Prior Publication Data

US 2008/0266559 A1 Oct. 30, 2008

Related U.S. Application Data

(63) Continuation-in-part of application No. 11/452,483, filed on Jun. 14, 2006, now Pat. No. 7,623,237.

(51) Int. Cl.
*G01J 4/00* (2006.01)
(52) U.S. Cl. ...................................... 356/369; 356/364
(58) Field of Classification Search .......... 356/364–369
See application file for complete search history.

(56) References Cited

U.S. PATENT DOCUMENTS

| | | | |
|---|---|---|---|
| 5,608,526 A | 3/1997 | Piwonka-Corle et al. | 356/369 |
| 5,910,842 A | 6/1999 | Piwonka-Corle et al. | 356/369 |
| 5,917,594 A | 6/1999 | Norton | 356/327 |
| 5,929,993 A | 7/1999 | Johs | 356/364 |
| 5,936,734 A | 8/1999 | Johs et al. | 356/364 |
| 5,963,327 A | 10/1999 | He et al. | 356/369 |
| 6,323,946 B1 | 11/2001 | Norton | 356/327 |
| 6,455,853 B2 | 9/2002 | Herzinger et al. | 250/341.4 |
| 6,583,877 B2 | 6/2003 | Norton | 356/369 |
| 6,734,967 B1 | 5/2004 | Piwonka-Corle et al. | 356/369 |
| 6,738,139 B1 | 5/2004 | Synowicki et al. | 356/369 |
| 7,636,161 B1 * | 12/2009 | Tiwald | 356/369 |
| 2002/0030813 A1 | 3/2002 | Norton | |
| 2004/0008349 A1 | 1/2004 | Norton | |
| 2004/0100632 A1 | 5/2004 | Piwonka-Corle et al. | |
| 2005/0105090 A1 | 5/2005 | Piwonka-Corle et al. | |

* cited by examiner

*Primary Examiner*—Gregory J Toatley, Jr.
*Assistant Examiner*—Iyabo S Alli
(74) *Attorney, Agent, or Firm*—James D. Welch

(57) ABSTRACT

A system for reducing reflections of a beam of electromagnetic radiation from the opposite, back, surface of an anisotropic sample, including methodology for investigating the incident, front, surface thereof with electromagnetic radiation, and analyzing the data as if the sample is isotropic.

15 Claims, 3 Drawing Sheets

ELLIPSOMETRIC INVESTIGATION OF ANISOTROPIC SAMPLES

CROSS REFERENCE TO OTHER APPLICATIONS

This application is a CIP of application Ser. No. 11/452,483 Filed Jun. 14, 2006 now U.S. Pat. No. 7,623,237, and therevia of Ser. No. 11/725,603 Filed Mar. 20, 2007 and therevia Claims Benefit from Provisional Application Ser. No. 60/691,297 Filed Jun. 17, 2005; and further Claims Benefit of Provisional Application Ser. 60/790,588 Filed Apr. 10, 2006.

TECHNICAL FIELD

The present invention relates to reduction of reflections of a beam of electromagnetic radiation from an opposite, back, surface of a sample, upon an incident, front, surface of which sample the beam impinges at an oblique or normal angle; and more particularly to a system and method for investigating an incident, front, surface of an anisotropic sample with electromagnetic radiation upon which it is incident, to provide data which can be analyzed as if the sample were isotropic.

BACKGROUND

It is known that when a beam of electromagnetic radiation is caused to impinge on the surface of a transparent or semi-transparent sample at an oblique or normal angle, reflected electromagnetic radiation from said sample generally contains components not only from the incident surface thereof, but also from the opposite, back, surface thereof. Especially where a sample investigated is anisotropic, the effect of said opposite, back, surface reflections can be difficult to model, and this makes characterization of the sample, or surface films thereupon, far more difficult, even essentially impossible. It is therefore desirable to reduce or eliminate the presence of said opposite, back, surface reflections while detecting electromagnetic radiation which reflects from an incident, front, surface thereof. It is disclosed that the identified problem can be present in systems where an anisotropic sample is elongated, such as a ribbon or sheet, and is continuously pulled over the means for supporting a sample, or in fixed position samples. Where said anisotropic sample and means for supporting it have different refractive indicies, opposite, back, surface reflections develop.

No known prior art addresses the problem where anisotropic samples are involved, however, regarding isotropic samples known approaches to reducing the problems caused by opposite, back, surface reflections generally include:
- mitigating opposite surface reflections by spatially separating said opposite, back, surface from the incident surface of a sample, (ie. use thick samples);
- the use a wedge shaped sample;
- roughen the opposite surface of the sample, (which it is noted is destructive and difficult on thin, brittle or soft samples), so that electromagnetic radiation incident thereupon is scattered rather than specularly reflected therefrom; and
- provide sample index matched material at said opposite, back, surface;
- account for opposite surface reflections via mathematical modeling.

It is noted that separating the incident (front) and opposite (back) surfaces of a sample does not work well if the diameter of the electromagnetic beam used in the sample investigation is larger than is the sample thickness. Focusing of a beam is, of course, possible to reduce its diameter at the point where it impinges on a sample, but this introduces a spread in the angle of incidence, which angular spread adds complexity and should be accounted for in a mathematical model of the sample. It is noted that accounting for opposite surface reflections via mathematical modeling introduces complexity into the model, and this is particularly troublesome where a sample is anisotropic in that different indicies of refraction are present as the sample is investigated along different axes. In general, it can be very difficult to completely model the effects an anisotropic sample has on beam polarization and/or intensity.

Known patents relevant to Back Surface Reflections are:
Patent to He et al., U.S. Pat. No. 5,963,327;
Patent to Johs, U.S. Pat. No. 5,929,993;
Patent to Synowicki, U.S. Pat. No. 6,738,139;
Patent to Johs et al. U.S. Pat. No. 5,936,734;
Patent to Herzinger et al. U.S. Pat. No. 6,455,853.

Other patents and Published Applications which were cited in Parent application Ser. No. 11/452,483 are:
U.S. Pat. No. 5,917,594;
U.S. Pat. No. 6,323,946;
U.S. Pat. No. 6,583,877;
U.S. Pat. No. 5,608,526;
U.S. Pat. No. 5,910,842;
U.S. Pat. No. 6,734,967;
Patent Application No. US 2002/030813;
Patent Application No. US 2004/008349;
Patent Application No. US 2004/100632;
Patent Application No. US 2005/105090.
Known Articles are:
"Surface Modification of Poly(ethylene terphthalata) Polymeric Films for Flexible Electronics Applications"; Laskarakis et al., Thin Solid Films, 516, (2008) 1443-1448.
"Diffraction for Anisotropic Random Rough Surfaces"; Zhao et al., Phys. Rev. B, Vol. 58, No. 11, 15 Sep. 1998.
"Suppression of Backside Reflections From Transparent Substrates"; Synowicki, Phys. Stat Sol. No. 5, 1085-1088, online Mar. 18, 2008.
"Engineering Properties of High Refractive Index Optical Gels for Photonic Device Applications"; Stone and Connor, Micro and Nano-photonic Materials and Devices, San Jose, Calif., 2000, Proc. SPIE, 3937, 144-155, (2000).
"On the Frustration of Back-surface Reflection from Transparent Substrates in Ellipsometry"; Hayton and Jenkins, Meas. Sci. Technol, 15, N17-N20 (2004), which describes suppression of back-surface reflections from a glass substrate by application of a soft, pliable semi-solid putty to the back side of said glass substrate. While relevant, this article does not disclose application to anisotropic samples but rather the glass substrate investigated was isotropic.

Need remains for a system which reduces the effect of reflections from the opposite, back, side of an anisotropic sample when electromagnetic radiation is caused to impinge on an incident, front, side thereof, at an oblique or normal angle of incidence, and improved methodology of investigating said samples.

DISCLOSURE OF THE INVENTION

Analysis of anisotropic samples based on ellipsometric data gathered by detecting reflected electromagnetic radiation therefrom, (which reflected electromagnetic radiation results from causing electromagnetic radiation to impinge on a sample surface at an oblique angle of incidence), can be difficult as propagation velocities of the electromagnetic radiation vary with direction in the bulk of the sample. In addition, where a sample is transparent to a wavelength, reflections of that wavelength from an opposite, back, surface of a sample which co-mingle with reflections from the incident, front, surface thereof, and can greatly complicate analysis of data produced by a detector thereof. The present invention provides an approach to investigation of samples which not only reduces the effect of opposite, back, surface reflections, by providing an index matched material at their opposite, back, surface, but by suppressing said opposite, back, surface reflections also suppresses the effect of complications resulting from sample anisotropy. The reason for this is that a beam of electromagnetic radiation which is caused to impinge on an interface between two materials that have the same, or nearly the same refractive index does not reflect therefrom, but continues as a transmitted beam which can be absorbed or scattered. It should be appreciated that where only reflections from the surface of an anisotropic sample, which are not subjected to sample anisotropic bulk properties are detected, analysis of the detected beam is simplified while valuable information about the anisotropic sample is collected.

It has been discovered that there are two necessary conditions for adequate suppression of sample opposite, back, surface reflections. The first is that there be good firm optical contact between the sample opposite, back, surface and the index matching material, (eg. no air bubbles present). Good optical contact ensures a good optical interface and index match everywhere under the measurement beam, which allows electromagnetic radiation to enter the index matched material rather than reflect from the interface between the sample opposite, back, surface and the index matching material. The second criteria is that electromagnetic radiation which enters the index matched material must become scattered, transmitted and/or absorbed before exiting said material. Scattering surfaces include rough surfaces, such as opaque tape, (eg. opaque electrical tape), or the back of translucent tape, (Scotch Magic tape), which is affixed to the opposite, back, surface of a sample, or can be effected via scattering by large particles in glues or paints which are applied to the opposite, back, surface of an anisotropic sample. A surprising result is how well the present invention methodology works over a wide range of wavelengths, (eg. at least 192 nm-2000 nm), even when index matching materials are not perfectly matched to the sample. This might be because opposite, back, surface reflection suppression is achieved by scattering, absorption effects and/or transmission effects, which compliment one another. One or another, or the effect of all effects being sufficient, at each wavelength, to provide the desired effect of preventing opposite backsurface effects from mixing with incident, front, surface effects which reach the detector, (of which it is believed that scattering is generally the more important effect). This view is substantiated by the fact that black opaque electrical tape, white glue or hand lotion, paint and translucent adhesive tape all work well.

A system for accomplishing the present invention results comprises:
  a source of a beam of electromagnetic radiation;
  an anisotropic sample;
  a means for supporting an anisotropic sample; and
  a detector of said beam of electromagnetic radiation.

Said means for supporting an anisotropic sample is present under said anisotropic sample near the location thereof whereat, during use, a beam of electromagnetic radiation provided by said source thereof is caused to impinge thereupon at an oblique or normal angle of incidence. Said means for supporting an anisotropic sample and said anisotropic sample can be characterized by a selection from the group consisting of:
  both having substantially matched indices of refraction; and
  the sample having a selection from the group consisting of:
    translucent adhesive tape;
    clear adhesive tape;
    double surface adhesive tape;
    opaque electrical tape;
    white glue;
    enamel paint;
    nail polish;
    vaseline;
    white hand lotion;
    toothpaste;
    super glue;
    rubber cement;
    grease;
    petroleum jelly;
    stick tack putty; and
    modeling clay etc.;
  having a refractive index being within a range of about 1.35-1.6 over a spectroscopic range being at least 192 nm-2000 nm; present at the interface between it and the means for supporting an anisotropic sample which is substantially index matched to that of said anisotropic sample, there being substantially uniform optical contact between the anisotropic sample and the index matching material such that electromagnetic radiation which enters the index matched material becomes scattered and/or absorbed before exiting said material and does not reflect back out of said sample to mingle with electromagnetic radiation reflected from the incident, front, of said sample.

It is noted that the first selection of providing both the sample and the means for supporting an anisotropic sample having substantially matched indices of refraction can be difficult to implement as a good contact therebetween might not result. Further, the use of water, clear glycerin lotion, gel-pak adhesive, adhesive paper post-it notes and black ink marker pen applied to the opposite, back, surface of an anisotropic sample do not provide good index matching results. This is indicated by the presence of reflected electromagnetic radiation from said sample opposite, back, surface when an oblique, or normal, angle of incidence beam of electromagnetic radiation is applied to the incident, front, surface sample.

Said anisotropic sample and said means for supporting an anisotropic sample can be variously rigid or flexible, and an important application of the present invention system is where relative motion therebetween is continuous. This can occur, for instance, where the anisotropic sample is a ribbon or sheet which is continuously pulled over the means for supporting a anisotropic sample. In such a case, said means for supporting an anisotropic sample can be a roller characterized by a selection from the group consisting of:
  it is rigid; and
  it is deformable.

For instance, where an anisotropic sample is rigid, benefit derives from using a deformable means for supporting an anisotropic sample in order to facilitate effecting a good contact therebetween. This point is less important, though not irrelevant however, where the anisotropic sample is flexible and can conform to the shape of said means for supporting an anisotropic sample, and/or in the case where translucent adhesive tape, clear adhesive tape, double surface adhesive tape, opaque electrical tape, white glue, enamel paint, nail polish, vaseline, white hand lotion, toothpaste, super glue, rubber cement, grease, petroleum jelly, stick tack putty, modeling clay, is caused to be present between said anisotropic sample and said means for supporting an anisotropic sample.

It is noted that index matching need not be perfect to achieve beneficial results. That is, it is only necessary to substantially suppress electromagnetic beam components which are influenced by the anisotropic sample, to provide utility. Where substantially all electromagnetic radiation reflecting from an anisotropic sample are from the surface thereof, (that is, where that amount of electromagnetic radiation reflecting from the opposite backsurface constitutes a small percentage of that from the incident, front, surface), analysis of the electromagnetic radiation reflecting from the incident front surface is less complicated. Specifically, it is disclosed that the method of the present invention has been found to work well over a spectroscopic range of 192 nm-2000 nm, for coated and uncoated samples with a refractive index over a range of 1.35-1.6. Examples investigated included an uncoated isotropic microscope slide, and anisotropic plastic sheets, a 100 micron thick anisotropic plastic bag, a 17 micron thick anisotropic plastic wrap, and an anisotropic polycarbonate CD-ROM disk.

A method of monitoring reflections of electromagnetic radiation caused to impinge on the incident, front, surface of an anisotropic sample at an oblique or normal angle of incidence, while substantially preventing opposite, back, surface reflections therefrom from complicating the results, comprises the steps of:
 a) providing a system comprising:
  a source of abeam of electromagnetic radiation;
  an anisotropic sample;
  a means for supporting an anisotropic sample; and
  a detector of said beam of electromagnetic radiation;

wherein said means for supporting an anisotropic sample is present under said anisotropic sample near the location thereof whereat, during use, a beam of electromagnetic radiation provided by said source thereof is caused to impinge thereupon at an oblique or normal angle of incidence;

said means for supporting an anisotropic sample and said anisotropic sample being characterized by a selection from the group consisting of:
 both having substantially matched indices of refraction; and
 the anisotropic sample having a selection from the group consisting of:
  translucent adhesive tape;
  clear adhesive tape;
  double surface adhesive tape;
  opaque electrical tape;
  white glue;
  enamel paint;
  nail polish;
  vaseline;
  white hand lotion;
  toothpaste;
  super glue;
  rubber cement;
  grease;
  petroleum jelly;
  stick tack putty; and
  modeling clay;
 having a refractive index being within a range of about 1.35-1.6 over a spectroscopic range being at least 192 nm-2000 nm; present at the interface between it and the means for supporting an anisotropic sample which is substantially index matched to that of said anisotropic sample, there being substantially uniform optical contact between the anisotropic sample and the index matching material such that electromagnetic radiation which enters the index matched material becomes scattered and/or absorbed before exiting said material and does not reflect back out of said sample to mingle with electromagnetic radiation reflected from the incident, front, of said sample;
 b) causing said source of a beam of electromagnetic radiation to provide a beam of electromagnetic radiation to impinge on a surface of said anisotropic sample, at an oblique or normal angle of incidence;
 c) monitoring electromagnetic radiation reflected from said anisotropic sample surface which enters said detector.

(Note, the means for supporting an anisotropic sample will typically contact a lower surface of an anisotropic sample at a location thereof which is substantially directly below where a beam of electromagnetic radiation is caused to impinge upon a top surface of said anisotropic sample in step b).

Said method can be further characterized by at least one selection from the group consisting of:
 storing at least some data provided by said data detector in machine readable media;
 analyzing at least some of the data provided by said data detector and storing at least some of the results of said analysis in machine readable media;
 displaying at least some data provided by said data detector by electronic and/or non-electronic means;
 analyzing at least some of the data provided by said data detector and displaying at least some of the results of said analysis by electronic and/or non-electronic means;
 causing at least some data provided by said data detector to produce a signal which is applied to provide a concrete and tangible result;
 analyzing at least some of the data provided by said data detector and causing at least some thereof to produce a signal which is applied to provide a concrete and tangible result.

It is also noted that if the anisotropic sample is elongated, the beam of electromagnetic radiation provided by said source thereof which is caused to impinge thereupon at an oblique or normal angle of incidence; can be directed along a locus which is selected from the group consisting of:
 parallel to the elongated dimension of said anisotropic sample;
 perpendicular to the elongated dimension of said anisotropic sample;
 between parallel and perpendicular to the elongated dimension of said anisotropic sample.

It is to be appreciated that a sample can be supported in a way that does not place a solid means for supporting directly thereunder, such as a split system that supports the sample on either side of a position at which the beam impinges. In that case the index matching is to the ambient atmosphere under the sample, or to a material affixed to the opposite, back, surface of the sample having a refractive index being within a range of about 1.35-1.6 over a spectroscopic range being at least 192 nm-2000 nm, examples of which were previously disclosed. Such a situation is to be considered to be within the scope of the Claims.

The present invention will be better understood by reference to the Detailed Description Section of this application, in combination with the Drawings.

DETAILED DESCRIPTION

Figure 1:
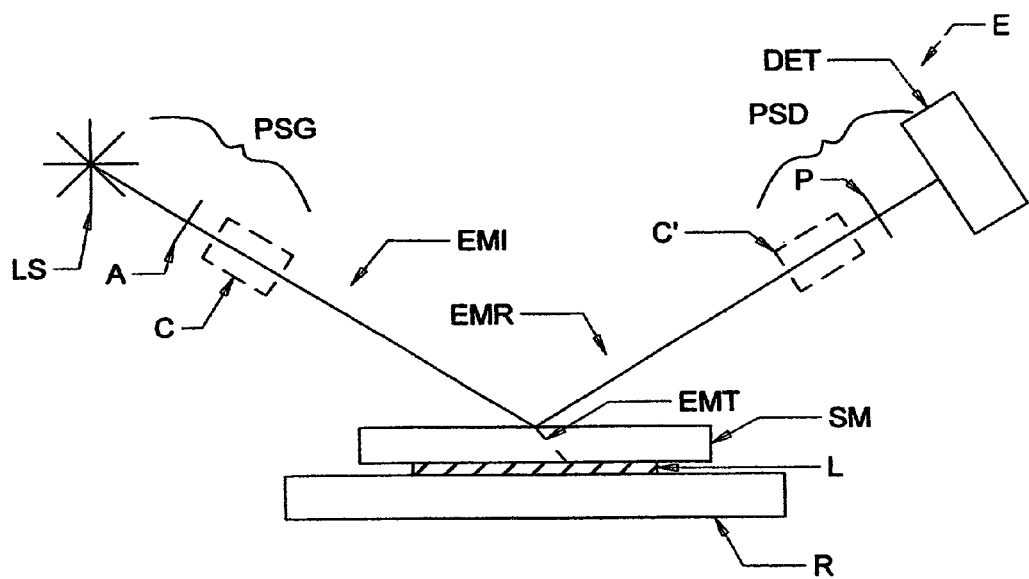
FIG. 1 shows a basic ellipsometer system with an anisotropic sample (SM) positioned on a means for supporting an anisotropic sample (R).

Turning now to FIG. 1, there is shown a basic ellipsometer system (E) with an anisotropic sample (SM) positioned on an essentially geometrically planar means for supporting (R) an anisotropic non-moving, sample (SM). Shown are a polarization state generator (PSG) which provides a beam of electromagnetic radiation (EMI) from a source thereof (LS) to said sample (SM) via a polarizer (P) and optional compensator (C), and a polarization state detector (PSD), including a detector (DET) for receiving of a beam of electromagnetic radiation (EMR) reflected from said sample (SM), via an analyzer (A) and optional compensator (C). Note also indication of a material (L) between the anisotropic sample (SM) and the means for supporting an anisotropic sample (R). Said material (L) is a distinguishing feature of the present invention as it is chosen to at least approximately index match to the anisotropic sample (SM) so that in use a portion of the incident beam (EMI) which transmits (EMT) through the sample (SM) does not reflect to the detector (DET) in reflected beam (EMR). Reflected beam (EMR) then, comprises substantially only components of (EMI) which reflect from the surface of the anisotropic sample (SM). This greatly simplifies analysis of data provided by the detector (DET) in response to received electromagnetic radiation (EMR).

Turning now to the Drawings, FIGS. 2-5 demonstrate anisotropic samples (SM) which can be investigated by the present invention system, including means to reduce opposite, back, surface reflections. Note that the anisotropic samples (SM) shown indicate that can be rigid or flexible and can comprise a moving elongated "ribbon". It is also shown that a means for supporting (R) said anisotropic sample (SM) can be a roller (R). The system is assumed to generally also comprise a source (LS) and detector (DET) as in FIG. 1 as part of polarization state generator (PSG) and polarization state detector (PSD). The systems in FIGS. 2-5 further show that:

said anisotropic sample (SM) has top (S1) and bottom (S2) surfaces;

there is a means for supporting (R) said anisotropic sample (SM) having an outer surface (S3); and said source (PSG) is shown as a polarization state generator of a beam of electromagnetic radiation (EMI) and said detector (PSD) is shown as being a polarization state detector and as receiving of a reflected beam of electromagnetic radiation (EMR).

Importantly, note that a portion of the beam (EMI) transits into the anisotropic sample as (EMT), and can reflect from an interface between said anisotropic sample (SM) and said means for supporting (R) said Sample (SM). Said means for supporting (R) an anisotropic sample (SM) is present under said anisotropic sample (SM) near the location thereof whereat, during use, a beam of electromagnetic radiation (EMI) provided by said source thereof is caused to impinge thereupon at an oblique or normal angle of incidence. Also note that said means for supporting (R) an anisotropic sample (SM) and said anisotropic sample (SM) are characterized by a selection from the group consisting of:

having substantially matched indices of refraction, (FIGS. 2 and 3); and having material (L), (FIGS. 4 and 5), present at the interface therebetween which is substantially index matched to that of said anisotropic sample (SM); where material (L) is to be interpreted to Include one or more selections from the group consisting of:
translucent adhesive tape;
clear adhesive tape;
double surface adhesive tape;
opaque electrical tape;
white glue;
enamel paint;
nail polish;
vaseline;
white hand lotion;
toothpaste;
super glue;
rubber cement;
grease;
petroleum jelly;
stick tack putty; and
modeling clay;

having a refractive Index being within a range of about 1.35-1.6 over a spectroscopic range being at least 192 nm-2000 nm.

Figure 2:
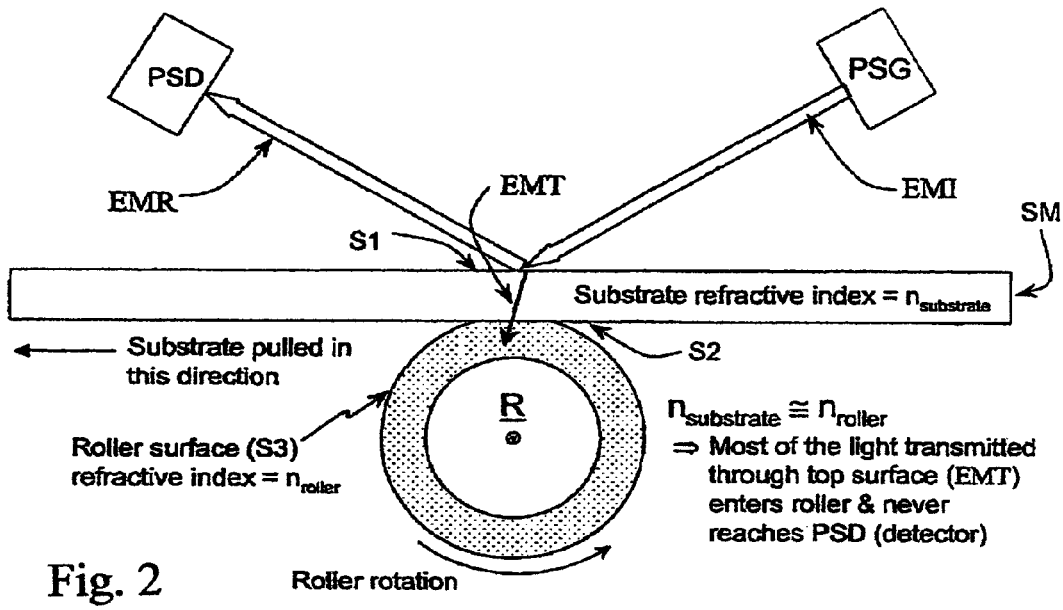
FIGS. 2 and 3 demonstrate present invention system means for supporting anisotropic samples, including means to reduce opposite, back, surface reflections, in combination with rigid and non-rigid anisotropic samples in place therewith, respectively, said anisotropic samples and means for supporting them being substantially index matched such that opposite, back, surface reflections are reduced when the anisotropic samples are investigated thereby.
Figure 3:
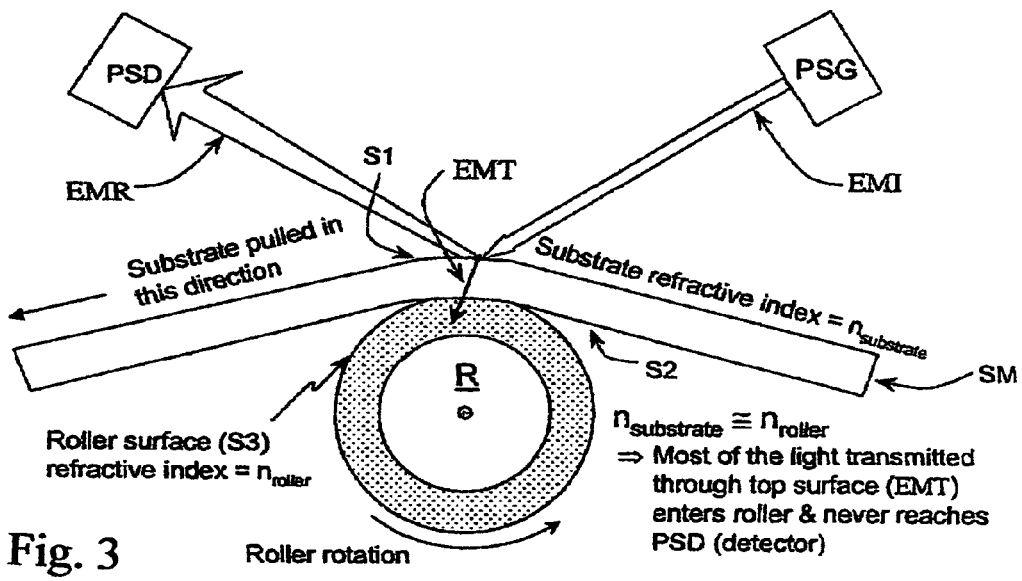
Figure 4:
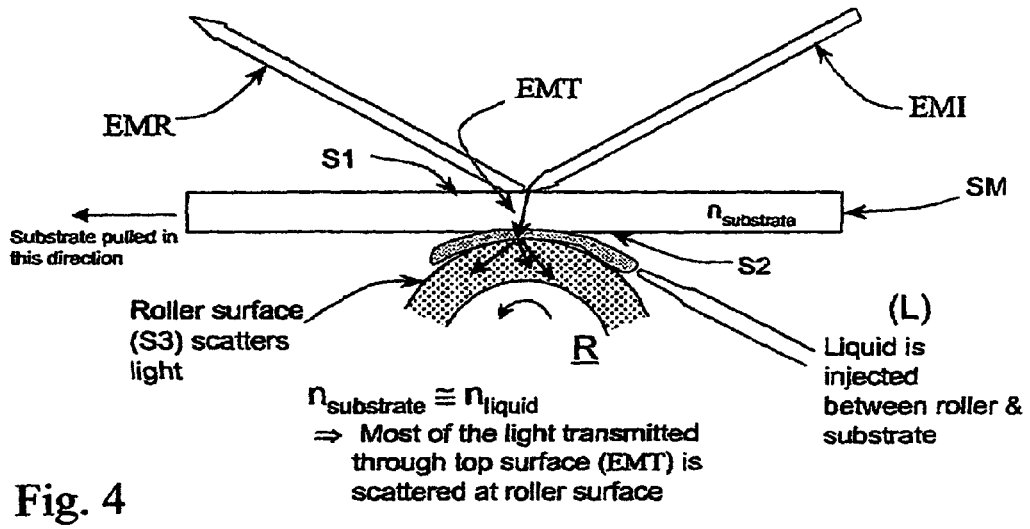
FIGS. 4 and 5 demonstrate present invention systems means for supporting anisotropic samples, including means to reduce opposite back surface reflections comprising an index matching material between said means for supporting anisotropic sample, and rigid and non-rigid anisotropic samples, respectively, such that opposite, back, surface reflections are reduced when the anisotropic samples are investigated thereby.
Figure 5:
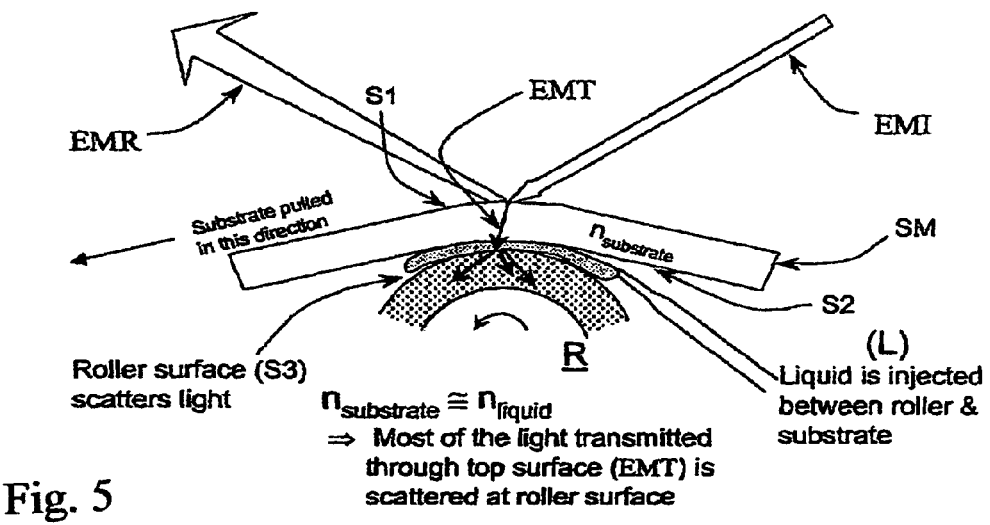

Said means for supporting (R) it, and/or said anisotropic sample (SM) can each be rigid, (see FIGS. 1, 2 and 4 which show a rigid anisotropic sample), or flexible, (see FIGS. 3 and 5 which show a flexible anisotropic sample (SM)). That is the anisotropic sample (SM) can be rigid or flexible, and independently the means for supporting (R) it can be rigid or flexible.

(It is noted that in the embodiments of FIGS. 4-5 an index matching material (L) is indicated as present and preferably comprising a liquid, when a sample moves. This is appropriate for the scenarios of FIGS. 4-5, but as particularly indicated in the FIG. 1 embodiment, it is to be understood that the index matching material is not limited to being a liquid but can instead be a solid. Also, as shown in FIGS. 1 and 2, the material (L) present in FIG. 1 can be removed altogether if the means for supporting (R) the anisotropic sample (SM) are index matched or if the anisotropic sample (SM) is rigid and the means for supporting (R) it is rigid).

A method of monitoring reflections of electromagnetic radiation caused to impinge on the surface of an anisotropic sample (SM) at an oblique or normal angle of incidence, while substantially preventing opposite, back, surface reflections therefrom from complicating the results, comprising the steps of:

a) providing a system comprising:
   a source (PSG) of a beam (EMI) of electromagnetic radiation;
   an anisotropic sample (SM);
   a means for supporting (R) an anisotropic sample (SM); and
   a detector (PSD) of said beam (EMR) of electromagnetic radiation;

wherein said means for supporting (R) an anisotropic sample (SM) is present under said anisotropic sample (SM) near the location thereof whereat, during use, a beam (EMI) of electromagnetic radiation provided by said source (PSG) thereof is caused to impinge thereupon at an oblique or normal angle of incidence;

said means for supporting (R) an anisotropic sample and said anisotropic sample being characterized by a selection from the group consisting of:
   both having substantially matched indices of refraction; and
   the anisotropic sample (SM) having a selection from the group consisting of:
      translucent adhesive tape;
      clear adhesive tape;
      double surface adhesive tape;
      opaque electrical tape;
      white glue;
      enamel paint;
      nail polish;
      vaseline;
      white hand lotion;
      toothpaste;
      super glue;
      rubber cement;
      grease;
      petroleum jelly;
      stick tack putty; and
      modeling clay etc.;
   having a refractive index being within a range of about 1.35-1.6 over a spectroscopic range being at least 192 nm-2000 nm; said index matching material (L) being present at the interface between it and the means for supporting an anisotropic sample which is substantially index matched to that of said anisotropic sample (SM);

b) causing said source (PSG) of a beam of electromagnetic radiation to provide a beam (EMI) of electromagnetic radiation to impinge on a surface of said anisotropic sample (SM), at an oblique or normal angle of incidence;

c) monitoring electromagnetic radiation reflected (EMR) from said anisotropic sample (SM) surface which enters said detector (PSD).

Said method can be practiced where with a means for supporting an anisotropic sample is deformable or rigid and/or where the anisotropic sample is flexible or rigid.

It is also to be understood that the (PSG) and (PSD) in FIGS. 2-5 can be rotated in position about a normal to the anisotropic sample (SM) through 0-360 degrees so that the plane formed thereby is oriented as shown, or in any such rotated position. That is, for instance, if the anisotropic sample is elongated, the beam of electromagnetic radiation provided by said source thereof which is caused to impinge thereupon at an oblique or normal angle of incidence; can be directed along a locus which is selected from the group consisting of:
   parallel to the elongated dimension of said anisotropic sample;
   perpendicular to the elongated dimension of said anisotropic sample;
   between parallel and perpendicular to the elongated dimension of said anisotropic sample.

Figure 6:
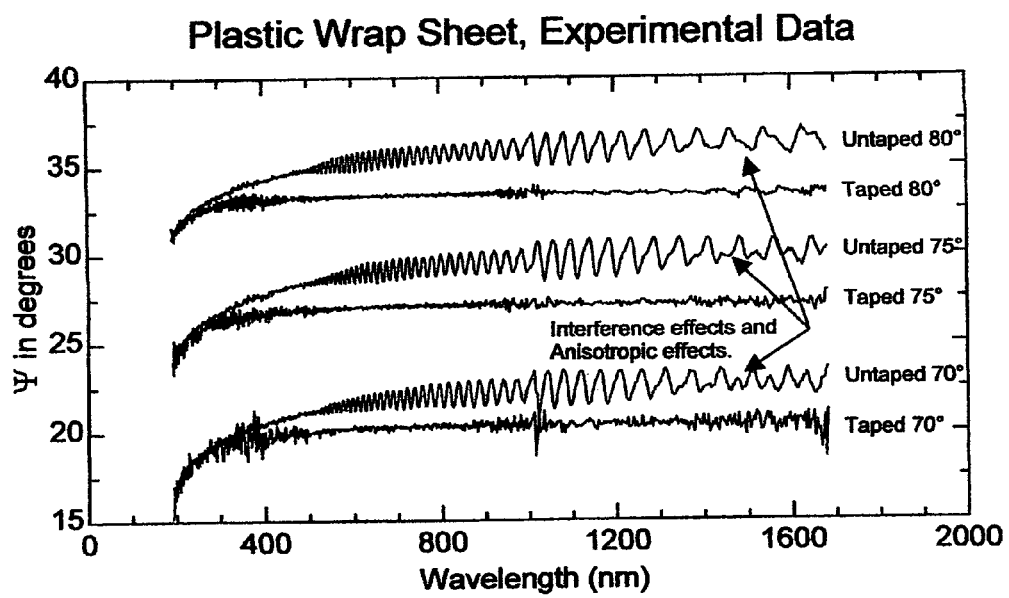
FIG. 6 shows Ellipsometric PSI data acquired from a 17 micron thick plastic wrap at multiple angles-of-incidence, with and without translucent tape present on the opposite, back, surface thereof.

To demonstrate the utility provided by the present invention, FIG. 6 shows Ellipsometric PSI ( ) data acquired from a 17 micron thick plastic wrap at multiple angles-of-incidence, (ie 70, 75 and 80 degrees), with (TAPED) and without (UNTAPED) translucent tape present on the opposite, back, surface thereof. Further, the presence of tape or other material helped to make the sample more rigid and easier to handle. Note that oscillations and an upward offset in the data, resulting from anisotropic effects and sample thickness, which are present in the data when tape is not present (UNTAPED), are removed when tape is present (TAPED). Analysis for the data acquired with the tape (TAPED) is present on the opposite, back, surface of the anisotropic sample, is similar to that for isotropic samples.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

I claim:

1. A system comprising:
   a source of a beam of electromagnetic radiation;
   an anisotropic sample;
   a means for supporting an anisotropic sample; and
   a detector of said beam of electromagnetic radiation;
wherein said means for supporting an anisotropic sample is present under said anisotropic sample near the location thereof whereat, during use, a beam of electromagnetic radiation provided by said source thereof is caused to impinge thereupon at an oblique or normal angle of incidence;
said means for supporting an anisotropic sample and said anisotropic sample being characterized by a selection from the group consisting of:
   both having substantially matched indices of refraction; and
   the anisotropic sample having a material present at the interface between it and the means for supporting an anisotropic sample which is substantially index matched to that of said anisotropic sample;
said system being characterized in that substantially uniform optical contact between the sample and the index matching material is achieved such that electromagnetic radiation which enters the index matched material becomes scattered and/or absorbed before exiting said index matched material and does not significantly reflect back out of said sample to mingle with electromagnetic radiation reflected from the incident, front, surface of said sample.

2. A system as in claim 1, wherein said means for supporting an anisotropic sample is rigid.

3. A system as in claim 1, wherein said means for supporting an anisotropic sample is deformable.

4. A system as in claim 1, wherein said sample is anisotropic and rigid.

5. A system as in claim 1, wherein said sample is anisotropic and flexible.

6. A system as in claim 1 in which the index matching material is a selection from the group consisting of:
- translucent adhesive tape;
- clear adhesive tape;
- double surface adhesive tape;
- opaque electrical tape;
- white glue;
- enamel paint;
- nail polish;
- vaseline;
- white hand lotion;
- toothpaste;
- super glue;
- rubber cement;
- grease;
- petroleum jelly;
- stick tack putty; and
- modeling clay;

having a refractive index being within a range of about 1.35-1.6 over a spectroscopic range being at least 192 nm-2000 nm.

7. A method of ellipsometrically investigating an anisotropic sample by monitoring reflections of electromagnetic radiation caused to impinge on an incident, front, surface of an anisotropic sample at an oblique or normal angle of incidence, while substantially preventing opposite, back, surface reflections therefrom from complicating the results, comprising the steps of:

a) providing a system comprising:
- a source of a beam of electromagnetic radiation;
- an anisotropic sample;
- a means for supporting an anisotropic sample; and
- a detector of said beam of electromagnetic radiation;

wherein said means for supporting an anisotropic sample is present under said anisotropic sample near the location thereof whereat, during use, a beam of electromagnetic radiation provided by said source thereof is caused to impinge thereupon at an oblique or normal angle of incidence;

said means for supporting an anisotropic sample and said anisotropic sample being characterized by a selection from the group consisting of:
- both having substantially matched indices of refraction; and
- the anisotropic sample having a selection from the group of index matching materials consisting of:
  - translucent adhesive tape;
  - clear adhesive tape;
  - double surface adhesive tape;
  - opaque electrical tape;
  - white glue;
  - enamel paint;
  - nail polish;
  - vaseline;
  - white hand lotion;
  - toothpaste;
  - super glue;
  - rubber cement;
  - grease;
  - petroleum jelly;
  - stick tack putty; and
  - modeling clay;

having a refractive index being within a range of about 1.35-1.6 over a spectroscopic range being at least 192 nm-2000 nm; present at the interface between it and the means for supporting an anisotropic sample, which material, is substantially index matched to that of said anisotropic sample, there being substantially uniform optical contact between the anisotropic sample and the index matching material such that electromagnetic radiation which enters the index matched material becomes scattered and/or absorbed before exiting said material and does not reflect back out of said sample to mingle with electromagnetic radiation reflected from the incident, front, surface of said sample;

b) causing said source of a beam of electromagnetic radiation to provide a beam of electromagnetic radiation to impinge on an incident, front, surface of said anisotropic sample, at an oblique or normal angle of incidence;

c) monitoring electromagnetic radiation reflected from said anisotropic sample surface which enters said detector;

said method being characterized by at least one selection from the group consisting of:
- storing at least some data provided by said data detector in machine readable media;
- analyzing at least some of the data provided by said data detector and storing at least some of the results of said analysis in machine readable media;
- displaying at least some data provided by said data detector by electronic and/or non-electronic means;
- analyzing at least some of the data provided by said data detector and displaying at least some of the results of said analysis by electronic and/or non-electronic means;
- causing at least some data provided by said data detector to produce a signal which is applied to provide a concrete and tangible result;
- analyzing at least some of the data provided by said data detector and causing at least some thereof to produce a signal which is applied to provide a concrete and tangible result.

8. A method as in claim 7 wherein said step of providing an anisotropic sample involves providing an anisotropic sample that is flexible.

9. A method as in claim 7 wherein said step of providing an anisotropic involves providing an anisotropic sample that is rigid.

10. A method as in claim 7 wherein said step of providing a means for supporting an anisotropic sample involves providing a means which is rigid.

11. A method as in claim 7 wherein said step of providing a means for supporting an anisotropic sample involves providing a means which is deformable.

12. A system as in claim 1, wherein the anisotropic sample is elongated and the beam of electromagnetic radiation provided by said source thereof which is caused to impinge thereupon at an oblique or normal angle of incidence; is directed along a locus which is selected from the group consisting of:
- parallel to the elongated dimension of said anisotropic sample;
- perpendicular to the elongated dimension of said anisotropic sample;
- between parallel and perpendicular to the elongated dimension of said anisotropic sample.

13. A method as in claim 7, wherein the anisotropic sample is elongated and the beam of electromagnetic radiation provided by said source thereof which is caused to impinge thereupon at an oblique or normal angle of incidence; is directed along a locus which is selected from the group consisting of:
- parallel to the elongated dimension of said anisotropic sample;

perpendicular to the elongated dimension of said anisotropic sample;

between parallel and perpendicular to the elongated dimension of said anisotropic sample.

14. A system as in claim 1 wherein the source of a beam of electromagnetic radiation is spectroscopic.

15. A system as in claim 14 wherein said spectroscopic source provides wavelengths over a range of about 192 nm-2000 nm.

* * * * *